United States Patent [19]

Blank

[11] Patent Number: 4,847,088

[45] Date of Patent: Jul. 11, 1989

[54] SYNERGISTIC ANTIMICROBIAL COMPOSITION

[75] Inventor: Lynne M. B. Blank, Brighton, N.Y.

[73] Assignee: Dow Corning Corporation, Midland, Mich.

[21] Appl. No.: 187,151

[22] Filed: Apr. 28, 1988

[51] Int. Cl.$^4$ ............................................. A01N 25/34
[52] U.S. Cl. ..................... 424/404; 424/78; 424/409; 424/443; 523/122
[58] Field of Search ................................. 424/404, 78

[56] References Cited

U.S. PATENT DOCUMENTS

| | | | |
|---|---|---|---|
| 3,560,385 | 2/1971 | Roth | 252/49.6 |
| 3,730,701 | 5/1973 | Isquith et al. | 71/67 |
| 3,794,736 | 2/1974 | Abbott et al. | 424/78 |
| 3,817,739 | 6/1974 | Abbott et al. | 71/67 |
| 3,860,709 | 1/1975 | Abbott et al. | 424/184 |
| 3,865,728 | 2/1975 | Abbott et al. | 210/169 |
| 4,034,079 | 7/1977 | Schoonman | 424/78 |
| 4,084,747 | 4/1978 | Alliger | 239/4 |
| 4,259,103 | 3/1981 | Malek et al. | 71/67 |
| 4,282,366 | 8/1981 | Eudy | 556/413 |
| 4,371,577 | 2/1983 | Sato et al. | 428/96 |
| 4,394,378 | 7/1983 | Klein | 424/184 |
| 4,395,454 | 7/1983 | Baldwin | 428/290 |
| 4,406,892 | 9/1983 | Eudy | 424/184 |
| 4,408,996 | 10/1983 | Baldwin | 8/490 |
| 4,411,928 | 10/1983 | Baldwin | 427/2 |
| 4,414,268 | 11/1983 | Baldwin | 428/289 |
| 4,425,372 | 1/1984 | Baldwin | 427/2 |
| 4,467,013 | 8/1984 | Baldwin | 428/289 |
| 4,500,337 | 2/1985 | Young et al. | 424/78 |
| 4,504,541 | 3/1985 | Yasuda et al. | 428/264 |
| 4,614,675 | 9/1986 | Ona et al. | 424/78 |
| 4,615,937 | 10/1986 | Bouchette | 428/288 |
| 4,631,297 | 12/1986 | Battice et al. | 521/78 |
| 4,692,374 | 9/1987 | Bouchette | 428/288 |
| 4,721,511 | 1/1988 | Kupits | 8/188 |
| 4,781,974 | 11/1988 | Bouchette | 428/288 |

FOREIGN PATENT DOCUMENTS

| | | |
|---|---|---|
| 156809 | 3/1985 | Japan. |
| 8601457 | 1/1987 | PCT Int'l Appl. . |
| 1386876 | 3/1975 | United Kingdom . |
| 1433303 | 4/1976 | United Kingdom . |

*Primary Examiner*—Thurman K. Page
*Assistant Examiner*—P. Prater
*Attorney, Agent, or Firm*—Jim L. DeCesare

[57] ABSTRACT

An antimicrobial agent and its use together with an acid provides a composition that possesses synergistic effects. More particularly, there is provided a synergistic antimicrobial composition in the form of a quaternary ammonium compound and an acid such as boric, citric, and malic.

8 Claims, No Drawings

SYNERGISTIC ANTIMICROBIAL COMPOSITION

BACKGROUND OF THE INVENTION

This invention relates to an antimicrobial agent and its use together with an acid to provide a composition that possesses synergistic effects. More particularly, the invention provides a synergistic antimicrobial composition in the form of a quaternary ammonium compound and an acid such as boric, citric, and malic.

Antimicrobial agents are chemical compositions that are used to prevent microbiological contamination and deterioration of products, materials, and systems. Particular areas of application of antimicrobial agents and compositions are, for example, cosmetics, disinfectants, sanitizers, wood preservation, food, animal feed, cooling water, metalworking fluids, hospital and medical uses, plastics and resins, petroleum, pulp and paper, textiles, latex, adhesives, leather and hides, and paint slurries. Of the diverse categories of antimicrobial agents and compositions, quaternary ammonium compounds represent one of the largest of the classes of agents in use. At low concentrations, quaternary ammonium type antimicrobial agents are bacteriostatic, fungistatic, algistatic, sporostatic, and tuberculostatic. At medium concentrations they are bactericidal, fungicidal, algicidal, and viricidal against lipophilic viruses. Silicone containing quaternary ammonium compounds are well known as exemplified by U.S. Pat. No. 3,560,385, and the use of such compounds as antimicrobial agents is taught, for example, in a wide variety of patents such as U.S. Pat. Nos. 3,730,701, and 3,817,739, where the compounds are used to inhibit algae; 3,794,736 and 3,860,709 where they are employed for sterilizing or disinfecting a variety of surfaces and instruments; 3,865,728, where the compounds are used to treat aquarium filters; 4,259,103; and in British Patent No. 1,386,876. Published unexamined European Application No. 228464 of July 15, 1987, teaches that microorganisms on plants can be killed by the application thereto of an aqueous mixture of a surfactant and an organosilicon quaternary ammonium compound. In a particular application of an antimicrobial silicone quaternary ammonium compound, a paper substrate is rendered resistant to the growth of microorganisms in U.S. Pat. No. 4,282,366. In U.S. Pat. No. 4,504,541, an antimicrobial fabric is disclosed which is resistant to discoloration and yellowing by treatment of the fabric with a quaternary ammonium base containing an organosilicone. U.S. Pat. No. 4,516,937, as well as its companion U.S. Pat. No. 4,692,374, relate to wet wiper towelettes having an antimicrobial agent substantive to the fibers of the web and being an organosilicon quaternary ammonium compound. In a series of Burlington Industries, Inc. U.S. Pat. Nos. 4,408,996, 4,414,268, 4,425,372, and 4,395,454, such compounds are disclosed to be useful in surgical drapes, dressings, and bandages. This same assignee also disclose these compounds as being employed in surgeons' gowns in U.S. Pat. Nos. 4,411,928 and 4,467,013. Organosilicon quaternary ammonium compounds have been employed in carpets, in U.S. Pat. No. 4,371,577; applied to walls, added to paints, and sprayed into shoes, in U.S. Pat. No. 4,394,378; applied to polyethylene surfaces and used in pillow ticking in U.S. Pat. No. 4,721,511; in flexible polyurethane foams of fine-celled, soft, resilient articles of manufacture in U.S. Pat. No. 4,631,297; and mixed with a surfactant in Japanese Kokai Application No. 58-156809, filed Aug. 26, 1983, of Sanyo Chemical Industries, Ltd., for the purpose of achieving uniformity of distribution of compounds to a surface. Thus the versatility of such compositions is readily apparent. It is not new to employ an acid to kill germs. U.S. Pat. No. 4,034,079, is representative of the use of boric acid. In U.S. Pat. No. 4,084,747, lactic acid is utilized. What is new and not believed to be taught in the prior art is the concept of combining such acids with the particular silanes of the present invention to kill germs synergistically. In accordance with the present invention, it has been found that antimicrobial properties of silicone containing quaternary ammonium compounds can be improved by mixing the antimicrobial agent with an acid to produce a composition that acts synergistically in preventing microbiological contamination and deterioration of products, materials, and systems. For example, 3-(trimethoxysilyl)-propyldimethyloctadecylammonium chloride is an effective antimicrobial agent in which the active ingredient hydrolyzes in water and reacts with substrates with which it is brought into contact. These substrates demonstrate nonleaching board spectrum antimicrobial activity. By including an acid component in the antimicrobial composition, such activity of this particular quaternary ammonium compound has been increased substantially against a mixed fungal culture where neither the acid nor the quaternary ammonium compound was effective alone. Hence, the compositions set forth in the present invention possess advantages over existing antimicrobial treating agents and provide improved results thereover, since the combinations disclosed herein of an antimicrobial agent together with an acid provide better results than when either of the individual components are employed separately. Thus, the disadvantages of the prior art are overcome with the present invention wherein improved antimicrobial agents are provided.

SUMMARY OF THE INVENTION

This invention relates to a synergistic antimicrobial composition formed by combining:

(a) a silane of the general formula $$Y_3SiRN^+R'R''R'''X^-$$

where y denotes an organic or a hydrolyzable radical, R denotes a divalent hydrocarbon radical with 1 to 6 carbon atoms, R', R'' and R''' independently denote saturated or unsaturated hydrocarbon radicals containing 1 to 18 carbon atoms, saturated or unsaturated organic radicals consisting of carbon, hydrogen and oxygen; carbon, hydrogen, and sulfur; or carbon, hydrogen and nitrogen, and X denotes an anion, with (b) an acid selected from the group consisting of acetic, adipic, anisic, benzoic, boric, butyric, capric, citraconic, citric, cresotinic, elaidic, formic, fumaric, gallic, glutaric, glycolic, lactic, lauric, levulinic, maleic, malic, malonic, oleic, oxalic, palmitic, phthalic, propionic, pyruvic, salicylic, stearic, succinic, tannic, and tartaric acids, and where the mole ratio of (a) to (b) is between about 1:1 and about 1:10.

The preferred acids are citric, boric, and malic, and the most desirable mole ratio of (a) to (b) is preferably about 1.5. The silanes are more particularly represented by the formula:

$$Y_3Si(CH_2)_mN^+(CH_3)_2(CH_2)_nCH_3X^-$$

where Y denotes an organic or hydrolyzable radical, X denotes an acid anion, and where m+n is 16 to 23, m is 1 to 11, and n is 9 to 17. Specific silanes are, for example,

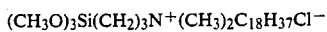

and

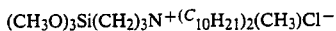

The invention also relates to a method of inhibiting the proliferation of potentially destructive microorganisms on a substrate by treating the substrate with an effective amount of a synergistic antimicrobial composition formed by combining the silane of the general formula indicated above together with an acid of the group set forth previously. The substrate is preferably paper.

The invention further relates to a cellulosic fiber substrate having a surface that inhibits the proliferation of potentially destructive microorganisms present on the substrate by treating the substrate with an effective amount of a synergistic antimicrobial composition formed by combining the silane of the general formula indicated previously together with an acid of the group set forth above.

It is therefore an object of the present invention to provide compositions, methods of treatment, and articles of manufacture, wherein there is employed a synergistic antimicrobial agent containing a silane and an acid.

It is also an object of the present invention to provide compositions, methods of treatment, and articles of manufacture, wherein there is employed a synergistic antimicrobial agent containing a silane such as 3-(trimethoxysilyl)propyldimethyloctadecylammonium chloride, and an acid such as one of citric, boric, and malic, for example.

These and other features, objects, and advantages, of the present invention will become apparent from the following detailed description of the invention.

DETAILED DESCRIPTION OF THE INVENTION

In order to illustrate the concept of the present invention, tests were conducted as set forth hereinbelow. Results from the tests are set forth in the form of tabular data in order to facilitate an understanding of the invention. Varied samples were prepared some of which acted as control samples, while others contained varied compositions of components selected such that the data could be better interpreted.

For example, in Table I, four samples were prepared containing the ingredients shown and in the amounts specified. The sole sample containing the acid component of the invention was Sample No. 4. These four samples were tested one against the other along with a control sample for the prevention of fungal overgrowth, and the results of these tests as well as the comparison between the various samples can be seen in Table II. Table II shows that the sole sample providing a zero percent fungal overgrowth was Sample No. 4 which is equivalent to the identically numbered sample in Table I, which is the acid containing composition of the present invention. Thus, it should be apparent that the inclusion of citric acid, for example, along with the antimicrobial quaternary ammonium compound indicated as "B" in the Tables produces a result not obtainable with either the acid component alone or the antimicrobial quaternary ammonium compound when used separately. For example, when used separately in Sample No. 2 in Table I, the quaternary ammonium compound "B" allowed 30% fungal overgrowth as shown in Table II. Sample No. 1 containing a cyclic antimicrobial quaternary ammonium compound of 3-(trimethoxysilyl)-propyloctadecyldimethyl ammonium chloride and 3-chloropropyltrimethoxysilane in methanol, was not as effective as the acid containing Sample No. 4, allowing a 75% fungal overgrowth. Sample No. 4 out performed a mixture of two antimicrobial agents in Sample No. 3 where the antimicrobial compound "B" was combined with another quaternary ammonium salt ARQUAD® T2, manufactured by Armour Hess Chemicals, allowing a fungal overgrowth of 75%. The blank control sample in Table II was ineffective allowing a 100% fungal overgrowth.

In view of the data obtained and set forth in Tables I and II, additional tests were conducted with samples of citric and boric acid to confirm the results of Table II. Thus, in Table III, varied samples were prepared and tested for the prevention of fungal overgrowth over a two to three week period. It can be seen from Table IV that the citric and boric acid compositions containing the antimicrobial compound "B" again out performed both the acids when employed alone, as well as the quaternary ammonium compound "B", when each were employed individually. Thus, over a two week period, there was no fungal overgrowth with both the mixtures of compound "B" with either citric or boric acid. Over the three week period, the mixture of boric acid and compound "B" outperformed the mixture of compound "B" with citric acid by 20%. In order to demonstrate the durability and the substantivity of the compounds of the present invention, it should be noted that the anion of an aqueous sodium salt of bromphenol blue can be complexed with the cation of a polymerized silane of this invention while it is on a substrate. The blue colored complex, substantive to a water rinse, is qualitatively indicative of the presence of the cation on the substrate thus indicating the extent of antimicrobial agent on a given substrate. A comparison of the intensity of retained blue color to a color standard is used as a check to determine if the treatment has been applied properly.

The method consists of preparing a 0.02 to 0.04 weight percent solution of bromphenol blue in distilled water. This solution is made alkaline using a few drops of saturated $Na_2CO_3$ solution per 100 milliliters of the solution. Two to three drops of this solution are placed on the treated substrate and allowed to stand for two minutes. The substrate is then rinsed with copious amounts of tap water and the substrate is observed for a blue stain and it is compared to a color standard.

For a spectrophotometric determination, the following test is used.

The sodium salt of bromphenol blue is depleted from a standard solution by complexing with the cations on a treated substrate. The change in bromphenol blue concentration is determined spectrophotometrically or by comparison with color standards whereby the level of substrate treatment by the cationic silane is determinable.

The method consists of preparing a 0.02 weight percent standard solution of bromphenol blue in distilled water. It is made alkaline with a few drops of saturated $Na_2CO_3$ solution per 100 milliliters of bromphenol blue solution. The color of this solution is purple.

The blank solution is adjusted to yield a 10 to 12% transmittance reading when measured in 1 cm cells using a spectrophotometer set at 589 nm by the following method.

Fill a container ¾ full of distilled water and add 2 ml of the 0.02% standard bromphenol blue solution for every 50 ml of distilled water. Add 0.5 ml of a 1% Triton ® X-100 surfactant (manufactured by Rohm and Haas, Philadelphia, PA, USA) aqueous solution for every 50 ml of water. Mix, and using the spectrophotometer, determine the maximum absorbance. Adjust the upper zero to 100% transmittance with distilled water. Check the percent transmittance of the working bromphenol blue solution at the maximum absorbance setting. Adjust the blank solution to 10 to 12% transmittance with either water or bromphenol blue standard solution as necessary.

The samples of treated substrate are tested by placing 0.5 gram samples of the substrate standards in a flask large enough for substantial agitation of the sample and the test solution. Add 50 ml of the working solution. Agitate for 20 minutes on a wrist-action shaker. Fill the test curvette with the test solution. Centrifuge if particulate matter is present. Measure the % transmittance at the wavelength set forth above. The transmittance is compared against a standard curve prepared by preparing several substrate samples of known concentration of the cationic silane. For example, samples containing a known amount of cationic silane at, for example, 0%, 0.25%, 0.50%, 0.75% and 1% are read spectrophotometrically and a curve is plotted. The data in Tables II and IV was generated using the following technique.

The antimicrobial activity of a treated surface was evaluated by shaking a sample weighing 0.75 grams in a 750,000 to 1,500,000 count *Klebsiella pneumoniae* suspension for a one hour contact time. The suspension was serially diluted, both before and after contact, and cultured. The number of viable organisms in the suspensions was determined. The percent reduction based on the original count was determined. The method was intended for those surfaces having a reduction capability of 75 to 100% for the specified contact time. The results are reported as the percent reduction.

Media used in this test were nutrient broth, catalog No. 0003-01-6 and tryptone glucose extract agar, catalog No. 002-01-7 both available from Difco Laboratories, Detroit, Mich., U.S.A. The microorganism used was *Klebsiella pneumoniae American Type Culture Collection; Rockville, Md. U.S.A.*, catalog No. 4352.

The procedure used for determining the zero contact time counts was carried out by utilizing two sterile 250 ml. screw-cap Erlenmeyer flasks for each sample. To each flask was added 70 ml of sterile buffer solution. To each flask was added, aseptically, 5 ml of the organism inoculum. The flasks were capped and placed on a wrist action shaker. They were shaken at maximum speed for 1 minute. Each flask was considered to be at zero contact time and was immediately subsampled by transferring 1 ml of each solution to a separate test tube containing 9 ml of sterile buffer. The tubes were agitated with a vortex mixer and then 1 ml of each solution was transferred to a second test tube containing 9 ml of sterile buffer. Then, after agitation of the tubes, 1 ml of each tube was transferred to a separate sterile petri dish. Duplicates were also prepared. Sixteen ml of molten (42° C.) tryptone glucose extract agar was added to each dish. The dishes were each rotated ten times clockwise and ten times counterclockwise. The dishes were then incubated at 37° C. for 24 to 36 hours. The colonies were counted considering only those between 30 and 300 count as significant. Duplicate samples were averaged. The procedure used for determining the bacterial count after 1 hour was essentially the same as that used to determine the count at the zero contact time. The only difference was that pour plating was performed at the $10^0$ and $10^{-1}$ dilutions as well as at the $10^{-2}$ dilution. "Percent reduction" was calculated by the formula $$\%R = \frac{\frac{B+C}{2} - A_{100}}{\frac{B+C}{2}}$$

where A is the count per milliliter for the flask containing the treated substrate; B is zero contact time count per milliliter for the flask used to determine "A" before the addition of the treated substrate and C is zero contact time count per milliliter for the untreated control substrate.

TABLE I

| | SAMPLE | | | |
|---|---|---|---|---|
| | I | II | III | IV |
| Water(gms.) | — | 539 | 539 | 533.5 |
| Temperature(°C.) | 61 | 61 | 61 | 61 |
| Time(min.) | 30 | 30 | 30 | 30 |
| Solution(gms.) | 550 | 550 | 550 | 550 |
| Paper(gms.) | 5 | 5 | 5 | 5 |
| Temp. Rise(°/min.) | 2 | 2 | 2 | 2 |
| Compound | A | B | B | B |
| Compound(gms.) | 550 | 11 | 5.5 | 5.5 |
| Acid | — | — | — | Citric |
| Acid(gms.) | — | — | — | 11 |
| Additive | — | — | C | — |
| Additive (gms.) | — | — | 5.5 | — |

A = Cyclic quaternary ammonium salt
B = $(CH_3O)_3Si(CH_2)_3N^+ (CH_3)_2C_{18}H_{37}Cl^-$
C = ARQUAD ® T2, a quaternary ammonium salt of Armour Hess Chemicals

TABLE II

| SAMPLE | FUNGAL (% Overgrowth) |
|---|---|
| Control | 100 |
| 1 | 75 |
| 2 | 30 |
| 3 | 75 |
| 4 | 0 |

TABLE III

| ACID | ACID (gms.) | WATER (gms.) | B (gms.) |
|---|---|---|---|
| Citric | 11 | 550 | 5.5 |
| Citric | 11 | 539 | — |
| Boric | 11 | 550 | 5.5 |
| Boric | 11 | 539 | — |
| — | — | 494 | 55 |

TABLE IV

| | FUNGAL (% Overgrowth) | |
|---|---|---|
| SAMPLE | TWO WEEKS | THREE WEEKS |
| Blank Control | 100 | 100 |
| Citric Acid Control | 100 | 100 |
| Citric Acid + B | 0 | 20 |
| Boric Acid Control | 10 | 10 |
| Boric Acid + B | 0 | 0 |
| Solution B | 90 | 90 |
| 10% Solution B | 90 | 90 |

The silanes useful in this invention also have the general formula

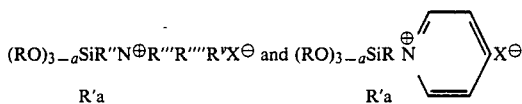 and 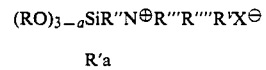

It should be noted that generically, these materials are quaternary ammonium salts of silanes. Most of the silanes falling within the scope of this invention are known silanes and references disclosing such silanes are numerous. One such reference, U.S. Pat. No. 4,259,103, issued to James R. Malek and John L. Speier, on Mar. 31, 1981, discusses the use of such silanes to render the surfaces of certain substrates antimicrobial. Canadian Patent No. 1,010,782, issued to Charles A. Roth shows the use of fillers treated with certain silanes to be used in paints and the like to give antimicrobial effects.

Numerous other publications have disclosed such silanes, namely, A. J. Isquith, E. A. Abbott and P. A. Walters, Applied Microbiology, December, 1972, pages 859–863; P. A. Walters, E. A. Abbott and A. J. Isquith, Applied Microbiology, 25, No. 2, p. 253–256, February 1973 and E. A. Abbott and A. J. Isquith, U.S. Pat. No. 3,794,736 issued Feb. 26, 1974, U.S. Pat. No. 4,406,892, issued Sept. 27, 1983, among others.

For purposes of this invention, the silanes can be used neat or they can be used in solvent or aqueous-solvent solutions. When the silanes are used neat, the inventive process is preferably carried out in a system in which some small amount of water is present. If it is not possible to have a system with some small amount of water present, then a water soluble or water-dispersable, low molecular weight hydrolyzate of the silane may be used. What is important is the fact that the durability of any effect produced by the silane as part of a product requires that the silane molecule react with a surface to a certain extent. The most reactive species, as far as the silanes are concerned, is the $\equiv$SiOH that is formed by hydrolysis of the alkoxy groups present on the silane. The $\equiv$SiOH groups tend to react with the surface and bind the silanes to the surface. It is believed by the inventor even though the prime mode of coupling to the surface system is by the route described above, it is also believed by the inventor that the alkoxy groups on the silicon atom may also participate in their own right to bind to the surface.

Preferred for this invention is a reactive surface containing some small amount of water. By "reactive", it is meant that the surface must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radicals. RO in the above formulas can also be R. R can also be hydrogen thus indicating the silanol form, i.e. the hydrolyzate. The value of a is 0, 1 or 2 and R' is a methyl or ethyl radical.

R" for purposes of this invention is an alkylene group of 1 to 4 carbon atoms. Thus, R" can be alkylene groups such as methylene, ethylene, propylene, and butylene. R"', R"", and R$^v$ are each independently selected from a group which consists of alkyl radicals of 1 to 18 carbons, —CH$_2$C$_6$H$_5$, —CH$_2$CH$_2$OH, —CH$_2$OH, and —(CH$_2$)$_x$NHC(O)R$^{vi}$. x has a value of from 2 to 10 and R$^{vi}$ is a perfluoroalkyl radical having from 1 to 12 carbon atoms. X is chloride, bromide, fluoride, iodide, acetate or tosylate.

Preferred for this invention are the silanes of the general formula

wherein R is methyl or ethyl; a has a value of zero, 1 or 2; R" is propylene; R"' is methyl or ethyl; R"" and R$^v$ are selected from alkyl groups containing 1 to 18 carbon atoms wherein at least one such group is larger than eight carbon atoms and x is either chloride, acetate or tosylate.

Most preferred for this invention are those silanes having the formula $(CH_3O)_3Si(CH_2)_3N^\oplus(CH_3)_2C_{18}H_{37}Cl^-$ and $(CH_3O)_3Si(CH_2)_3N^\oplus CH_3(C_{10}H_{21})_2Cl^-$.

As indicated above, most of these silanes are known from the literature and methods for their preparation are known as well. See, for example, U.S. Pat. No. 4,282,366, issued Aug. 4, 1981; U.S. Pat. No. 4,394,378, issued July 19, 1983, and U.S. Pat. No. 3,661,963 issued May 9, 1972, among others.

Specific silanes within the scope of the invention are represented by the formulae:
(CH$_3$O)$_3$Si(CH$_2$)$_3$N+(CH$_3$)$_2$C$_{18}$H$_{37}$Cl$^-$,
(CH$_3$O)$_3$Si(CH$_2$)$_3$N+(CH$_3$)$_2$C$_{18}$H$_{37}$Br$^-$,
(CH$_3$O)$_3$Si(CH$_2$)$_3$N+(C$_{10}$H$_{21}$)$_2$CH$_3$Cl$^-$,
(CH$_3$O)$_3$Si(CH$_2$)$_3$N+(C$_{10}$H$_{21}$)$_2$CH$_3$Br$^-$,
(CH$_3$O)$_3$Si(CH$_2$)$_3$N+(CH$_3$)$_3$Cl$^-$,
(CH$_3$O)$_3$SiCH$_2$CH$_2$CH$_2$P+(C$_6$H$_5$)$_3$Cl$^-$,
(CH$_3$O)$_3$SiCH$_2$CH$_2$CH$_2$P+(C$_6$H$_5$)$_3$Br$^-$,
(CH$_3$O)$_3$SiCH$_2$CH$_2$CH$_2$P+(CH$_3$)$_3$Cl$^-$,
(CH$_3$O)$_3$SiCH$_2$CH$_2$CH$_2$P+(C$_6$H$_{13}$)$_3$Cl$^-$,
(CH$_3$)$_3$Si(CH$_2$)$_3$N+(CH$_3$)$_2$C$_{12}$H$_{25}$Cl$^-$,
(CH$_3$)$_3$Si(CH$_2$)$_3$N+(C$_{10}$H$_{21}$)$_2$CH$_3$Cl$^-$,
(CH$_3$)$_3$Si(CH$_2$)$_3$N+(CH$_3$)$_2$C$_{18}$H$_{37}$Cl$^-$,
(CH$_3$O)$_3$Si(CH$_2$)$_3$N+(CH$_3$)$_2$C$_4$H$_9$Cl$^-$,
(C$_2$H$_5$O)$_3$Si(CH$_2$)$_3$N+(CH$_3$)$_2$C$_{18}$H$_{37}$Cl$^-$,
(CH$_3$O)$_3$Si(CH$_2$)$_3$N+(CH$_3$)$_2$CH$_2$C$_6$H$_5$Cl$^-$,
(CH$_3$O)$_3$Si(CH$_2$)$_3$N+(CH$_3$)$_2$CH$_2$CH$_2$OHCl$^-$,

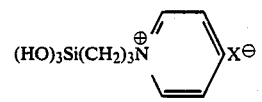

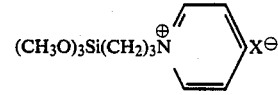

(CH$_3$O)$_3$Si(CH$_2$)$_3$N+(CH$_3$)$_2$(CH$_2$)$_3$NH-C(O)(CF$_2$)$_6$CF$_3$Cl$^-$,
(CH$_3$O)$_3$Si(CH$_2$)$_3$N+(C$_2$H$_5$)$_3$Cl$^-$.
In the above structures X is chlorine.

It should be noted that carriers may be employed herein such as gels, powders, creams and lotions, emulsions, microemulsions, and solvent solutions, of the active antimicrobial agents. Surfaces that can be treated include carpet; fabrics, for example socks, clothing, shoe inner liners, towels, bedding, upholstery, curtains, and draperies; as well as hard surfaces, for example walls, tables, ceilings, and furnishings.

While the treated substrates of the present invention are of general application, they are especially useful in the preparation of papers employed in conjunction with foodstuffs. Thus, the treated papers and substrates are useful as milk containers and cartons, field transport containers for fruit and vegetables, cardboard fruit containers, consumer foodstuff containers and wrappings, wrapping paper for fruit, vegetables, and meat, and as wrappers for soap, for example.

It will be apparent from the foregoing that many other variations and modifications may be made in the structures, compounds, compositions, and methods described herein without departing substantially from the essential concepts of the present invention. Accordingly, it should be clearly understood that the forms of the invention described herein are exemplary only and are not intended as limitations on the scope of the present invention.

That which is claimed is:

1. A synergistic antimicrobial composition comprising a mixture of
   (a) an organosilane having the general formula selected from the group consisting of

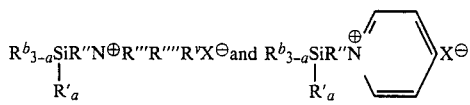

wherein, in each formula,
   $R^b$ is R or RO where each R is an alkyl radical of 1 to 4 carbon atoms or hydrogen;
   a has a value of 0, 1 or 2;
   R' is a methyl or ethyl radical;
   R" is an alkylene group of 1 to 4 carbon atoms;
   R''', R'''' and $R^v$ are each independently selected from a group consisting of alkyl radicals of 1 to 18 carbon atoms, $-CH_2C_6H_5$, $-CH_2CH_2OH$, $-CH_2OH$, and $-(CH_2)_xNHC(O)R^{vi}$, wherein x has a value of from 2 to 10 and $R^{vi}$ is a perfluoroalkyl radical having from 1 to 12 carbon atoms;
   X is chloride, bromide, fluoride, iodide, acetate or tosylate; and
   (b) an acid selected from the group consisting of acetic, adipic, anisic, benzoic, boric, butyric, capric, citraconic, citric, cresotinic, elaidic, formic, fumaric, gallic, glutaric, glycolic, latic, lauric, levulinic, maleic, malic, malonic, oleic, oxalic, palmitic, phthalic, propionic, pyruvic, salicylic, stearic, succinic, tannic, and tartaric acids; and where the mole ratio of (a) to (b) is between about 1:1 and about 1:10.

2. The composition of claim 1 wherein the acid is citric acid.

3. The composition of claim 2 wherein the mole ratio of (a) to (b) is about 1:5.

4. The composition of claim 1 wherein the acid is boric acid.

5. The composition of claim 1 wherein the silane is represented by the formula

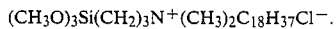

6. The method of inhibiting the proliferation of potentially destructive microorganisms on a substrate comprising treating the substrate with an effective amount of the synergistic antimicrobial mixture of claim 1.

7. The method of claim 6 wherein the substrate is paper.

8. A cellulosic fiber substrate having a surface that inhibits the proliferation of potentially destructive microorganisms present on the substrate, the surface being formed by treating the substrate with an effective amount of the synergistic antimicrobial mixture of claim 1.

* * * * *